US006856915B2

(12) United States Patent
Nishigaki et al.

(10) Patent No.: US 6,856,915 B2
(45) Date of Patent: Feb. 15, 2005

(54) METHODS OF IDENTIFYING ORGANISM BASED ON ITS GENOTYPE

(75) Inventors: Koichi Nishigaki, Saitama (JP); Tsutomu Takasawa, Nagano (JP); Keiichi Hamano, Chiba (JP)

(73) Assignee: Taitec Corporation, Saitama (JP)

( * ) Notice: Subject to any disclaimer, the term of this patent is extended or adjusted under 35 U.S.C. 154(b) by 0 days.

(21) Appl. No.: 09/841,157

(22) Filed: Apr. 25, 2001

(65) Prior Publication Data

US 2002/0192648 A1 Dec. 19, 2002

(30) Foreign Application Priority Data

Apr. 25, 2000 (JP) ........................................ 2000-123755

(51) Int. Cl.[7] ........................... G01N 33/48; C12Q 1/68
(52) U.S. Cl. ............................................. 702/19; 435/6
(58) Field of Search ................................. 702/19; 435/6, 435/4, 91 T; 703/11; 530/23.1, 24.3 T, 25.3 T; 436/94; 204/450 T

(56) References Cited

U.S. PATENT DOCUMENTS 6,228,586 B1 * 5/2001 Messier et al. ................. 435/6

OTHER PUBLICATIONS

Nishigaki et al. Structural analysis of nucleic acids by precise denaturing gradient gel electrophoresis: I. Methodology. J Biochem (Tokyo). Feb. 1992, vol. 111, No. 2, pp. 144–150.*

Nishigaki et al. Structural analysis of nucleic acids by precise denaturing gradient gel electrophoresis: II. Applications to the analysis of subtle and drastic mobility changes of oligo– and polynucleotides. Biochem (Tokyo). Feb. 1992, vol. 111, No. 2, pp.*

Nishigaki et al. DNA Profiling. An approach of systemic characterization, classification, and comparison of genomic DNAs. Chem. Lett. 1991, pp. 1097–1100.*

Pena et al. Sequence–specific "gene signatures" can be obtained by PCR with single specific primers at low stringency. PNAS Mar. 1994, vol. 91, pp. 1946–1949.*

Pena, et al. Proc. Natl. Acad. Sci. USA 91:1946–1949. 1994.*

Rolleke, et al., Applied and Environmental Microbiology 62(6):2059–2065. 1996.*

Pleissner, et al, Electrophoresis 20:755–765. 1999.*

Biyani and Nishigaki, "Hundredfold productivity of genome analysis by introduction of microtemperature–gradient gel electrophoresis", Electrophoresis, vol. 22, Issue 1, (2001), pp. 23–28.

Nishigaki et al., "Genome Profiling: A Realistic Solution for Genotype–Based Identification of Species", J. Biochem, 128 (2000), pp. 107–112.

* cited by examiner

Primary Examiner—Ardin Marschel
(74) Attorney, Agent, or Firm—Jacobson Holman PLLC

(57) ABSTRACT

A method for identifying a microorganism, wherein the method comprises the steps of: 1) preparing one or more kind(s) of double-stranded DNA fragments by the random PCR using at least a part of a genome of an organism of interest, 2) applying the double-stranded DNA fragments which were prepared in step 1 to temperature gradient gel electrophoresis (TGGE) or denaturant gradient gel electrophoresis (DGGE), 3) extracting identification dots of each DNA fragment from the electrophoresis pattern which was obtained in step 2, 4) determining PaSS and/or genome semi-distance from the identification dots which were obtained in step 3, and 5) analyzing the PaSS and/or genome semi-distance which were/was obtained in step 4, wherein pseudo-absolute position of identification dots is determined by the locational relation to standard DNA in the presence of standard DNA as the starting dots in TGGE or DGGE.

24 Claims, 3 Drawing Sheets

(a)     (b)

METHODS OF IDENTIFYING ORGANISM BASED ON ITS GENOTYPE

BACKGROUND OF THE INVENTION

1. Field of the Invention

The present invention relates to a method for identifying a species or homology of an organism such as microorganism by its genotype.

2. Description of the Related Art

Organisms which include microorganisms have been identified so far basically using their phenotypes. However, identification by phenotypes was not suited for distinguishing organisms more accurately. Particularly, there was practical limitation upon identifying/specifying microorganisms comprising a large number of species by phenotypes. Our daily life is surrounded by microorganisms. Microorganisms such as *Escherichia coli* 0157, *Mycobacterium tuberculosis*, methicillin-resistant *Staphylococcus aureus* (MRSA), and *Vibrio cholera* cause many diseases, and a technique for accurately identifying microorganisms is needed for establishing effective treatments and specifying infection pathways. It is also recognized that soil bacteria are involved in the productivity and quality of an agricultural product, and that the human health is greatly influenced by the enteric bacterial flora. Accurate studies have not carried out, however, concerning the relation between the productivity or quality of an agricultural product and the kind, quantity, and combination of soil bacteria, and the relation between the human health and the enteric bacterial flora. This is due to the fact that it is impossible to accurately identify/distinguish microorganism(s) by the conventional identification by its/their phenotype(s).

In the above-mentioned situation, identification of microorganisms by genotypes is proposed instead of that of phenotypes.

It is quite possible to identify/distinguish microorganism (s) by comparing the (whole) genome of each microorganism using the recent sequencing technique level. It needs, however, a significant amount of work and time, and is not a simple method. Therefore, identifying/distinguishing species of microorganisms by comparing the (whole) genome is practically not a widely applicable method. Although a method for comparing a part of a genome is known as a more simple method, enough information is not obtained for identifying/distinguishing species by comparing the 16S rRNA sequences.

SUMMARY OF THE INVENTION

It is therefore the object of the present invention to provide a method for identifying the species, homology, and so on of organisms such as microorganisms, which is simple to some extent and practically workable, and is based on genotypes.

The present invention is directed to a method for identifying an organism comprising the steps of:

1) preparing one kind or more of double-stranded DNA fragments by the random PCR using, as a template, at least a part of a genome of an organism which is to be identified,
2) subjecting the double-stranded DNA fragments prepared in step 1 to temperature gradient gel electrophoresis (TGGE) or denaturant gradient gel electrophoresis (DGGE),
3) extracting identification dots of each DNA fragment from an electrophoretic pattern which was obtained in step 2,
4) determining PaSS and/or genome distance(s) from the identification dots which were obtained in step 4, and
5) analyzing the PaSS and/or genome semi-distance(s) which was/were obtained in step 4, wherein in the electrophoresis by TGGE or DGGE, a standard DNA is co-existed as a standard point for the identification dots and the pseudo-absolute location of the identification dots is determined from the locational relation to the standard DNA.

BRIEF DESCRIPTION OF THE DRAWINGS

The above and other objects, aspects, features and advantages of the present invention will become more apparent from the following detailed description when taken in conjunction with the accompanying drawings, in which.

Figure 1:
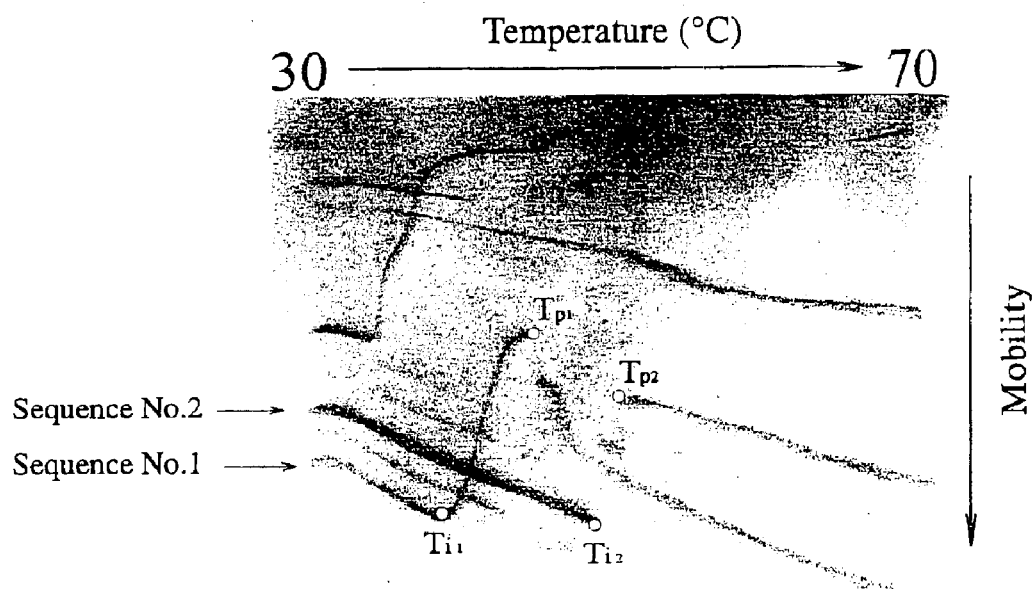
FIG. 1 illustrates examples of genome profiling images (an electrophores is pattern which is obtained by TGGE of standard DNAs which are shown by Seq. ID Nos. 1 and 2)

DESCRIPTION OF THE PREFERRED EMBODIMENTS (1) Preparation of Double-stranded DNA Fragments from Genome by Random PCR The random PCR is a method which was developed by the inventors.

The normal polymerase chain reaction (PCR) method is a method for amplifying a specific DNA region by repeating DNA synthesis using two kinds of primer which sandwich a specific DNA region and DNA polymerase. Specifically, 1) a double-stranded DNA is denatured by heat treatment at 90° C. or so to give single-stranded DNAs (denaturing), 2) a primer attaches to the obtained single-stranded DNA by annealing at 50° C. or so, and 3) a DNA chain is synthesized by DNA polymerase using the primer as the starting point using the single-stranded DNA as a template using monomer nucleotides as raw materials at 65° C. or so (elongation of strand). Only a double-stranded DNA fragment is amplified which corresponds to a sequence in a specific DNA region which was sandwiched between parts which have sequences which are complementary to the two kinds of primer by repeating a cycle comprising the denaturing, the annealing, and the elongation.

The above-mentioned PCR method is a method for amplifying only a DNA fragment in a specific DNA region. Therefore, the condition for the above-mentioned annealing is designed so that the primer can bind to a specific part of a single-stranded DNA which has a sequence which is complementary to the sequence of the primer (e.g., a pair of G and C or a pair of A and T). Namely, the condition for the annealing is designed so that a primer and a single-stranded DNA can form a double strand without causing a mismatch between the primers and the single-stranded DNA as a template. DNA strand can be amplified even by carrying out the above-mentioned annealing at about 30° C. and carrying out the elongation of strand at about 50° C. However, the temperature for the annealing is low, so that mismatch(es) (i.e., not complementary; e.g., a pair comprising G and A) can be contained in a part of the base pairs between a primer and a single-stranded DNA as a template. Normally, only a DNA fragment which has a absolutely complementary sequence can be a primer and allows amplifying the strand. On the contrary, if the annealing and the elongation are carried out at a relatively low temperature as described above, even a DNA fragment which does not have a completely complementary sequence can be a primer and allows amplifying the stand.

Therefore, if a cycle comprising denaturing, annealing, and elongation (wherein annealing and elongation are carried out at a lower temperature than the normal PCR) is repeated using DNA such as genome DNA as a template using a DNA fragment which has a specific sequence (e.g., a fragment which is 12mer or so, and is selected independent of a DNA sequence of a template) as a primer, even a DNA fragment which does not have a completely complementary sequence can be a primer, and the strand is amplified, so that one kind or more of double-stranded DNA fragment which can contain mismatch (es) in a primer part is/are formed. The purpose of this method is not to amplify a specific region on a template, and a strand is amplified if it can be a starting point for the elongation even if mismatches are contained to some extent, so that two kinds or more of double-stranded DNA fragment can be formed. In addition, it is found that if the same DNA which is used as the template and the same DNA fragment which is used as a primer and the same cycle conditions for denaturing and annealing are used, DNA strand(s) which has/have the same sequence(s) is/are always amplified. This method is called 'Random PCR' because the purpose of the method is not to amplify a specific region on a template.

By the random PCR, various DNA strands can be obtained in amplification by using a primer DNA fragment different in a sequence even if the same genome DNA is used as a template, or by changing the condition for the cycle of denaturing, annealing, and elongation. Especially obtained DNA strand(s) is/are largely changed by both length and sequence of the primer, so that it is preferable to choose an appropriate primer. Versatile sequence information of a genome can be taken out by changing a nucleotide sequence of a primer taking advantage of the character.

A method according to the present invention allows amplifying and preparing one or more kind(s) of double-stranded DNA fragment by the random PCR using as a template at least a part of a genome of a microorganism whose species and other properties are to be identified. At least a part of a genome which is used as a template in the random PCR can be prepared from a microorganism according to generally used methods. At least a part of a genome which is used in the random PCR as a template can be prepared, for example, by the alkali method (H. Wang, M. Gin, A. J. Cutler, Nucl. Acids Res., 21, 4153 (1993)).

The random PCR in which an obtained genome is used as a template can be carried out as follows:

Apart from the normal PCR method, an appropriate sequence, length and kind of a primer can be appropriately selected for the random PCR. Experimentally and analytically the most simple system, however, is the case where a relatively short single primer is used. Even in the case a single primer is used, and a genome which is derived from the same microorganism is amplified, a kind and quantity of a double-stranded DNA fragment which can be amplified depend on the sequence and length of the primer. In addition even in the case a single primer and a primer which has the same sequence and length are used, a kind and quantity of a double-stranded DNA fragment which can be amplified depend on the microorganism from which the genome is derived. Considering these facts, sequence, length, and kind of a primer are appropriately selected. Too long primer can have the hair-pin structure, can prevent annealing, and tends to lower a yield of a PCR product. Too short primer does not adequately stabilize a bonding containing mismatch (es), and tends to lower a yield of a PCR product. A length (base length) of a primer is suitably, for example, 8–20, preferably 10–16, more preferably 10–12, and most preferably 12. An oligonucleotide which has a length of 12 bases can be used as a primer. Such oligonucleotide primers include pfM4 (dCAGTCAGGACGT), (SEQ ID NO: 3), pfM12 (dAGAACGCGCCTG) (SEQ ID NO: 4), pfM14 (dCGTCGCTATTAA) (SEQ ID NO: 5), pfM19 (dCAGGGCGCGTAC) (SEQ ID NO: 6), $(dA)_{12}$ (dAAAAAAAAAAAA) (SEQ ID NO: 7), $(dA_3T_3)_2$ (dAAATTTAAATTT) (SEQ ID NO: 8), $(dAATT)_3$ (dAATTAATTAATT) (SEQ ID NO: 9), $(dACG)_4$ (dACGACGACGACG) (SEQ ID NO: 10), $(dAT)_6$ (dATATATATATAT) (SEQ ID NO: 11), $(dC)_{12}$ (dCCCCCCCCCCCC) (SEQ ID NO: 12), $(dCCGG)_3$ (dCCGGCCGGCCGG) (SEQ ID NO: 13), $(dG)_{12}$ (dGGGGGGGGGGGG) (SEQ ID NO: 15), $(dGA)_6$ (dGAGAGAGAGAGA) (SEQ ID NO: 16), $(dGGCC)_3$ (dGGCCGGCCGGCC) (SEQ ID NO: 17), (dCT)6 (dCTCTCTCTCTCT) (SEQ ID NO: 14), $(dT)_{12}$ (dTTTTTTTTTTTT) (SEQ ID NO: 18), $(dT_3G_3)_2$ (dTTTGGGTTTGGG) (SEQ ID NO: 19), $(dTGC)_4$ (dTGCTGCTGCTGC) (SEQ ID NO: 20), $(TA)_4C_2AC$ (dTATATATACCAC) (SEQ ID NO: 21), Cohesive1 (dGGGCGGCGACCT) (SEQ ID NO: 22), Cohesive2 (dAGGTCGCCGCCC) (SEQ ID NO: 23), 4sand (dGGGGTCGAGGGG) (SEQ ID NO: 24), $GCTA_9$ (dGCTAAAAAAAAA), (SEQ ID NO: 25), notG (dCAATTCTACAAC) (SEQ ID NO: 26), notT (dACGAGCGAGCGC) (SEQ ID NO: 27), Promote1 (dTATAATTATAAT) (SEQ ID NO: 28), Promote2 (dATTATAATTATA) (SEQ ID NO: 29), SD1 (dGATCACCTCCTTA) (SEQ ID NO: 30), SD2 (dTAAGGAGGTGATC) (SEQ ID NO: 31), Telomere1 (dCCCACCCACCCA) (SEQ ID NO: 32), Telomere2 (dTGGGTGGGTGGG) (SEQ ID NO: 33), FITC17-H-3' (5' GAGGAAACAGCTATGAGATCT TCTC 3'), (SEQ ID NO: 34), FITC17-H-5' (5' CAG GAA ACA GCT ATG ACG TTC TCA C 3'), (SEQ ID NO: 35), LH-7-3' (5' GGC GAT ATC CCT GAA A 3'), (SEQ ID NO: 36), LH-7-5' (5' TAT TAT TTC CGC AAA G 3') (SEQ ID NO: 37), M13 Reverse (5' CAG GAA ACA GCT ATG AC 3') (SEQ ID NO: 38), cy3-pfM12 (5' cy3-AGA ACG CGC CTG 3') (SEQ ID NO: 39) (with cy3 fluorescence), FITC/UCS (5' FITC-CA GGA AAC AGC TAT GAC 3') (SEQ ID NO: 40) (with FITC fluorescence), MA1-FITC (5' FITC-TGC TAC GTC TCT TCC GAT GCT GTC TTT CGC T 3') (SEQ ID NO: 41) (with FITC fluorescence), cy3-MA1 (5' cy3-TGC TAC GTC TCT TCC GAT GCT GTC TTT CGC T 3') (SEQ ID NO: 42) (with cy3 fluorescence), HEX-pfM11 (5' HEX-GAA CCT CCC GAC 3') (SEQ ID NO: 43) (with Hex fluorescence), TAM-TGC4 (5' TAM-TGC TGC TGC TGC 3') (SEQ ID NO: 44) (with Tamara fluorescence), and the like.

In the random PCR, as described above, PCR is operated at a remarkably lower temperature than the normal PCR while other operational conditions for the random PCR are substantially the same as the normal PCR. Reaction mixture and reaction condition for the random PCR are as follows: 100 μl of reaction mixture contains 200 μM dNTP (N=G, A, T, C), 0.5 μM primer, 10 mM Tris-HCl (pH 9.0), 50 mM KCl, 2.5 mM MgCl$_2$, 0.1% Triton X-100, 0.02 unit/μl Taq DNA polymerase, and an appropriate amount (e.g., 3 μl of a DNA solution which was prepared in a way which is described elsewhere is added and the total volume of the reaction mixture was adjusted to 100 μl) of template DNA. PCR comprises 20–30 cycles of the following steps: treatment at 94° C. for 1 min, denaturation at 94° C. for 30 min, annealing at 28° C. for 2 min, and elongation at 47° C. for 2 min, followed by treatment at 47° C. for 2 min. When pfM14 which has a low G+C content is used as a primer, annealing can be carried out at 23° C., elongation can be carried out at 42° C. for 10 min, and the final chase treatment can be carried out at 42° C. for 10 min. For the experiment which was described above, it is preferable to carry out preparation and mixing of the reaction mixture on a clean bench, and to irradiate UV light (312 nm for 10 min) to a solution (which contains all except template DNA) immediately before adding template DNA to prevent formation of PCR products which are derived from impurities.

For the above-mentioned random PCR, DNA labeled with a fluorescent marker can be amplified by using a raw material with a fluorescent marker. In this case, using a fluorescence labeled DNA as a standard DNA, identification dots (as described below) can be extracted by means of the image processing using fluorescence markers carried by the DNAs. A primer or nucleotide can be the raw material labeled with a fluorescent marker. A primer or nucleotide labeled with a fluorescent marker can be purchased or easily synthesized according to well known methods.

(2) Electrophoresis of Double-stranded DNA Fragment by TGGE or DGGE

According to the present invention, the double-stranded DNA fragments obtained in (1) are subjected to temperature gradient gel electrophoresis (TGGE) or denaturant gradient gel electrophoresis (DGGE).

Both TGGE and DGGE are well known methods. TGGE is described in detail, for example, in R. Riesner, et al., Electrophoresis 10, 377–389 (1989). DGGE is described in detail, for example, in E. S. Abrams, V. P. Stanton, Jr., Methods Enzymol., 212, 71 (1992). Both methods can be carried out easily using commercial apparatus. Both TGGE and DGGE are two-dimensional electrophoresis using a slab-type gel providing a temperature gradient or denaturant concentration gradient along and vertically to the electrophoresis direction of the double-stranded DNA. TGGE and/or DGGE allows understanding the behavior of melting (dissociation of two strands) which is characteristic to the nucleotide sequence of the double-stranded DNA. Namely, the strength (heat resistance or denaturant resistance) of bond of base pairs in a region which exists in the double-stranded DNA to be subjected to electrophoresis can be visualized by TGGE or DGGE.

For TGGE, a temperature gradient from 30° C. to 70° C. is normally applied. For DGGE, a denaturant such as urea and formamide can be used with a concentration gradient, for example, from 0 to 15M.

For a method according to the present invention, the pseudo-absolute position of an identification dot is determined from the locational relation to standard DNA which is added as a standard point for the identification dot upon electrophoresis by TGGE or DGGE. With the double-stranded DNA which was amplified by the random PCR, the standard DNA is co-existed as the standard dot for the identification dot, and then the mixture is subjected to electrophoresis, whereby the standard DNA also give an electrophoresis pattern corresponding to its sequence. The pseudo-absolute position of the identification dot of each double-stranded DNA can be determined from the locational relation to the electrophoresis pattern of the standard DNA. The standard DNA can be a kind of an inner standard specimen. Using such standard DNA allows analyzing data, which are obtained by the electrophoresis and have deviation to some extent depending on the condition, based on the same standard. Namely, using standard DNA allows correcting data which are obtained from electrophoresis pattern and normalizing them.

In electrophoresis by TGGE or DGGE, at least a part of double-stranded DNA has the melting-starting dot, the slowest dot (a dot where a migration speed becomes slowest), and the SS mobility-conversing dot (a dot where the migration speed is conversed to that of a single-stranded DNA) as featuring points. These featuring points cannot be observed under a given condition for electrophoresis. It is preferable that standard DNA allows clearly observing featuring points such as the melting-starting point, the slowest point, and the SS mobility-conversing point under an adopted electrophoresis condition for giving a standard point. In addition, it is preferable that the standard DNA gives a pattern which can be easily distinguished from that of double-stranded DNA which is derived from the genome which is to be identified.

Standard DNA should be a set of DNA (double-stranded DNA, hair pin-type DNA/RNA, or the like) which gives clear transition near each of both ends, for example, within a predetermined temperature gradient (or concentration gradient), and be one which is not overlapped in the transition range of 200–1,000 base long for normally observing the transition. Two kinds or more of standard DNA can be used for providing more accurate standard point(s).

Not only a sequence shown by SEQ ID Nos. 1 or 2 in Sequence Listing but also other sequences can be used for standard DNA.

Electrophoresis patterns which were obtained by TGGE with standard DNAs of SEQ ID Nos. 1 and 2 are illustrated in FIG. 1, and their properties are summarized in Table 1. The condition for the above-mentioned TGGE was as follows: an electrophoresis apparatus (Taitec TG-180, manufactured by Taitec, Japan), 4% polyacrylamide gel (8M urea, 40 mM Tris buffer (pH8.0)), linear temperature gradient from 30° C. to 70° C., 300V, and 90 min.

TABLE 1

|  |  | SEQ No. 1 | SEQ No. 2 |
| --- | --- | --- | --- |
| Restored temperature | $T_i$ (° C.) | 60 | 70 |
|  | $T_p$ (° C.) | 67 | 72 |

(3) Extraction of Species Identification Dot from Electrophoresis Pattern

Bands (electrophoresis pattern) of DNA (including standard DNA) on an electrophoresis gel which were obtained by TGGE or DGGE are visualized, for example, by silver staining, and identification dots are extracted from each visualized pattern.

Silver staining of the gel can be carried out, for example, according to Boulikas and Hancock (T. Boulikas, R. Hancock, J. Biochem. Biophys. Methods, 5, 219 (1981)) with an improvement using PEG treatment according to Ohsawa and Ebata (K. Ohsawa, N. Ebata, Anal. Biochem., 135, 409 (1983)).

The method will be outlined below:
1) Gel which is attached to a gel bond film is transferred to a plastic container which contains 200 ml of a 30% PEG2000 aqueous solution, and the obtained mixture is stirred at room temperature (15–30° C.) for 30 min. Meanwhile the gel is separated from the film, is shrunk, and becomes white and translucent.
2) The solution is once substituted for 150 ml of distilled water, and the gel is rinsed adequately. This procedure is repeated twice. The rinsed liquid is completely sucked with an aspirator.
3) After the rinsed liquid is removed, about 200 ml of silver stain solution (10 ml of 1M NaOH and 2 ml of 25% ammonia are added to 200 ml of bidistilled water, and mixed, and 0.4 g of silver nitrate is added to the mixture) is poured, and the resultant mixture is stirred.
4) The stain solution is substituted for 200 ml of bidistilled water, and the water is stirred for 1 min, and the water is discarded, and this procedure is repeated again.
5) The liquid is substituted for about 200 ml of a developer (which was prepared by adding 200 $\mu$l of 10% citric acid and 200 $\mu$l of formalin to 200 ml of bidistilled water, followed by mixing), and the gel is gently shaken until the bands are stained so as to have appropriate density.
6) When the bands are stained so as to have appropriate density, the developer is quickly removed, and 200 ml of a stop solution which was previously prepared (10% acetic acid+40% methanol, in water) is added, and the gel and the liquid are shaken for about 10 min to give a stained gel specimen (the waste developer should not be dried because explosive fulminating silver can be formed).

Several ng of DNA fragments (if it is 21 ng and 300 base long, it is about 10 fmol, i.e., $6 \times 10^9$ molecules) which exist in 100 $\mu$l of PCR solution can be easily detected by the treatment above (even one-tenth of that can be detected under a good condition).

In case an enough amount of DNA is available (several tens ng/band), EtBr (ethidium bromide) method can be applied, i.e., a gel after electrophoresis is washed with water, soaked in a 5 $\mu$g/ml EtBr solution (for about 10 min), and directly observed under a UV lamp (at about 360 nm).

Alternately, species identification dots can be extracted by means of a fluorescent marker carried by DNA, i.e., by using a raw material labeled with a fluorescent marker for random PCR to amplify DNA labeled with the fluorescent marker in the amplification process by random PCR of step 1. The raw material with a fluorescent marker can be a primer or nucleotide which becomes a substrate for DNA polymerase. Both a primer labeled with a fluorescent marker and a polynucleotide labeled with a fluorescent marker are well-known, and are easily commercially available.

Using a raw material for random PCR, for example, a primer labeled with a fluorescent marker, subjecting to electrophoresis DNAs which were separately amplified using fluorescent markers being different in excitation and fluorescence wavelengths on one plate, and using an excitation wavelength and a fluorescence wavelength which have different patterns for each DNA allows separately detecting each of the DNAs. Specifically, the obtained amplified DNA can be detected using primers A, B, and C for amplifying DNAs of organisms a, b, and c, respectively, which belong to different species one another, wherein primers A, B, and C have the same sequence, but have different fluorescent markers, using an excitation wavelength and a fluorescence wavelength corresponding to the fluorescent marker of primer A with respect to organism a; using an excitation wavelength and a fluorescence wavelength corresponding to the fluorescent marker of primer B with respect to organism b; and using an excitation wavelength and a fluorescence wavelength corresponding to the fluorescent marker of primer B with respect to the organism c allow detection of each DNA. Alternately, amplification of DNAs of an organism is made by using primers A, B, and C which are different in the sequence and fluorescent marker and the obtained amplified DNAs can be detected using an excitation wavelength and a fluorescence wavelength corresponding to the fluorescent marker of primer A; using an excitation wavelength and a fluorescence wavelength corresponding to the fluorescent marker of primer B; and using an excitation wavelength and a fluorescence wavelength corresponding to the fluorescent marker of primer C.

Herein 'identification dots' refers to inflection dot, isomobility dot, and the like which each pattern (curve) has.

Identification dots (e.g., inflection dot and isomobility dot) can be chosen, for example, in the following way:
1) A dot where melting begins ($T_i$) is determined as the maximal value of second derivative or the middle dot between two dots which give second derivatives of 0.
2) A discontinuous dot (dot which gives a large change in Y for a slight increase in X) is determined to give $T_{min}$ (minimal mobility dot).
3) Dot Tc where a DNA arrives at a mobility of a single-stranded state (dot where a DNA first arrives at the final mobility) is determined.

The above-mentioned operation comprising steps 1–3 is carried out from a clear band by turns to give, for examples, 10–12 dots as a whole although the number of band can be appropriately chosen. If the species is already known and the band which corresponds to the species is known, the above-mentioned operation can be carried out with the previously specified band(s).

Specifically, identification dot(s) can be extracted by the image processing using a CCD camera and a computer. For the image processing, an image of an electrophoresis pattern which was visualized by the above-mentioned silver staining is imported via an appropriate means for taking picture into an appropriate electric recording medium as a color image or a gray-scale image. Specifically, an image of an electrophoresis pattern can be imported into a computer as a genome profiling image using a means for taking picture such as digital camera. FIG. 1 illustrates an example of genome profiling image of a sequence for inner standard as described below.

Genome profiling images are normalized on a computer, if necessary, after distortion is corrected. Correcting distortion can be omitted if the distortion of a genome profiling image is within a normal error range. Normalization is the image processing in which ordinate (Y-axis; mobility) and abscissa (X-axis; temperature or concentration) directions are normalized based on species identification dots of an inner standard reference specimen, experimental condition parameters, and so on. This normalization makes mobility M dimensionless so as to have a value from 0 to 1. For temperature T, effective temperature which is obtained by converting a denaturation efficiency of urea which is present in a gel into temperature, i.e., restored temperature is applied.

After normalization, lines are extracted, and the extracted lines are functionalized. Lines (bold lines) are extracted by so-called ream-forming reference dot shift method with respect to each of some bands in genome profiling images. In case a band of interest is continuous before and after denaturation, a bold line can be extracted by specifying a dot on the band. In case a band of interest is discontinuous before and after denaturation, however, a bold line is extracted by specifying two dots before and after denaturation. A bold line can also be extracted using the binarization method instead of the ream-forming reference dot shift method.

A bold line corresponding to each band which was extracted from a genome profiling image is then slimmed. Slimming is a process in which a bold line is converted into a slimmed line which is a single-valued function. In slimming, a slimmed line is obtained which consists of smooth chain (curve) which consists of many centers of gravity by the smoothing process in which an average coordinate of Y-coordinate of an gravity and Y-coordinate of two adjacent gravities is replaced for the Y-coordinate of the gravity, for example, by the running average method.

The slimmed line is functionalized. In the functionalization, each slimmed line is approximated to an n-order function which has an appropriate order (e.g., ten-order) or trigonometric function using, for example, the Newton-Rapson method.

Featuring points were extracted for slimed lines and for each band curve which has been functionalized. Extracted featuring points include melting-initiation point $P_{ini}$, minimal mobility point $P_{min}$, and mobility end point $P_{end}$. Melting-initiation point is a point on a band curve which corresponds to the initiation of melting before denaturation. Minimal mobility point $P_{min}$ is a point on a band curve at which the mobility reaches the minimum. Mobility end point $P_{end}$ is a point on a band curve at which a DNA reaches the mobility in a single-stranded state after denaturation.

Figure 2:
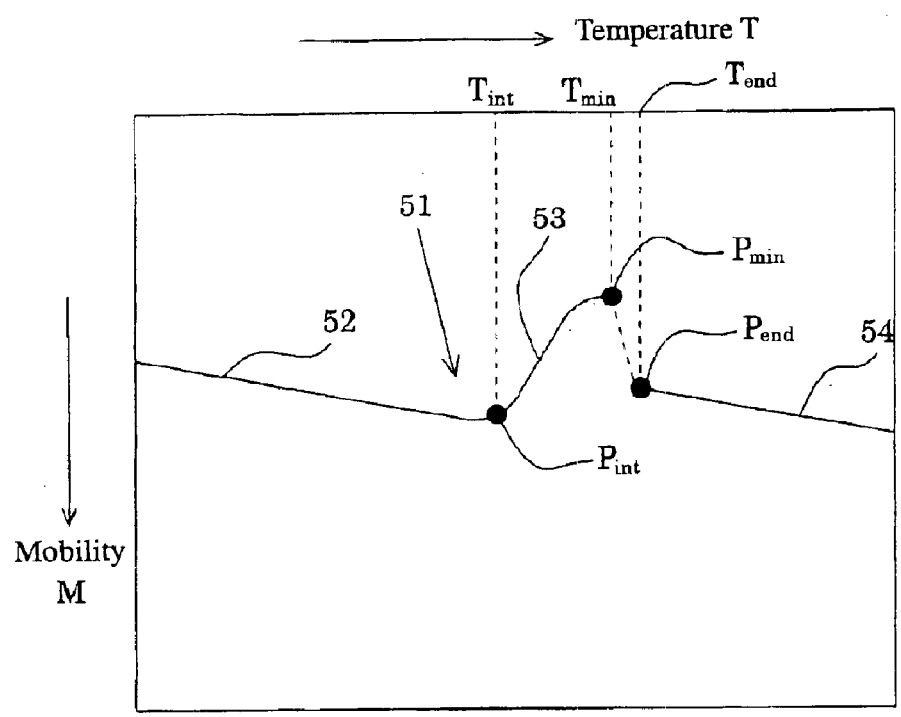
FIG. 2 illustrates the first typical band curve.

FIG. 2 illustrates a mode of the first typical band curve.

As shown in FIG. 2, in typical first band curve 51, mobility M increases nearly linearly with temperature T at lower than the temperature ($T_{ini}$) at which the melting begins. The temperature reaches the temperature ($T_{ini}$) which corresponds to melting initiation point $P_{ini}$, melting began, and mobility M decreases nearly linearly with temperature T, and the decreasing rate is slowly decreased, and a DNA reaches minimal mobility point $P_{min}$.

After the temperature reaches the temperature ($T_{min}$) which corresponds to minimal mobility point $P_{min}$, mobility M rapidly increases with the increase in the temperature, and a DNA reaches the mobility in a single-stranded state after denaturation, i.e., mobility end $P_{end}$. At a temperature higher than the temperature ($T_{end}$) which corresponds to mobility end point $P_{end}$, mobility M increases nearly linearly with temperature T again. It is considered to be due to the decrease in the viscosity accompanied with the increase in the temperature, but substantially not due to the change in the shape. It is frequently observed that minimal mobility point $P_{min}$ becomes a discontinuous point, and a band curve becomes discontinuous between the temperature ($T_{min}$) which corresponds to minimal mobility point $P_{min}$ and a temperature which is slightly lower than the temperature ($T_{end}$) which corresponds to mobility end point $P_{end}$.

Figure 3:
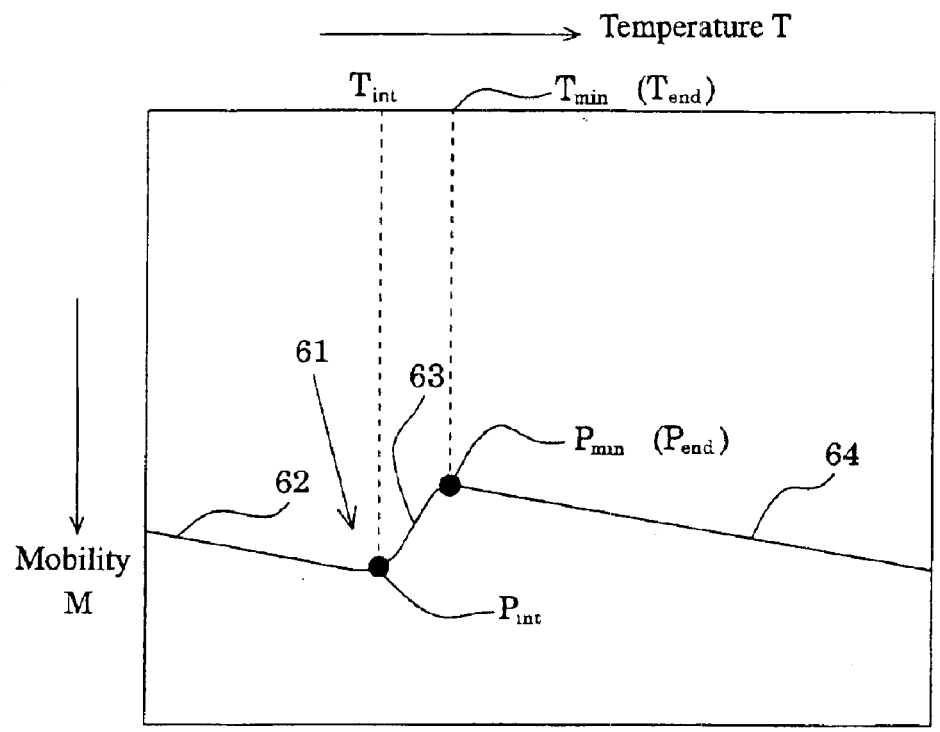
FIG. 3 illustrates the second typical band curve.

FIG. 3 illustrates a shape of the second typical band curve.

As shown in FIG. 3, in typical second band curve 61, as similarly as in the case of first band curve 51, mobility M increases nearly linearly with temperature T at a temperature which is lower than the temperature ($T_{ini}$) at which melting begins, and the temperature reaches the temperature ($T_{ini}$) which corresponds to melting initiation point $P_{ini}$, and melting begins, and mobility M decreases nearly linearly with temperature T. Apart from the case of first band curve 51, however, after a DNA reaches minimal mobility point $P_{min}$, mobility M increases nearly linearly with temperature T again at a temperature which is higher than the temperature ($T_{min}$) which corresponds to minimal mobility point $P_{min}$. Namely, in second band curve 61, minimal mobility point $P_{min}$ and mobility end point $P_{end}$ conform, so that a band curve does not become discontinuous.

Based on the information such as the first differentiation, the second differentiation, and its discontinuous points of band curves which were obtained via functionalization, featuring points such as melting initiation point $P_{ini}$, minimal mobility point $P_{min}$, and mobility end $P_{end}$ are extracted.

Specifically, melting initiation point $P_{ini}$ is extracted as the middle point of a curve part which is surrounded by two straight line parts 52 (62) and 53 (63). Hence, melting initiation point $P_{ini}$ is determined based on the first differentiation value and the second differentiation value of band curve 51 (61).

Minimal mobility point $P_{min}$ is extracted, for example, as discontinuous points on a curve in the case of first band curve 51. On the other hand, in the case of second band curve 61, minimal mobility point $P_{min}$ is determined as the same point as mobility end point $P_{end}$ as described later.

In addition, mobility end point $P_{end}$ is determined as a dot which departs from the straight line part 54 (64) as observed along -x direction based on the first differentiation value and the second differentiation value of band curve 51 (61).

Figure 4:
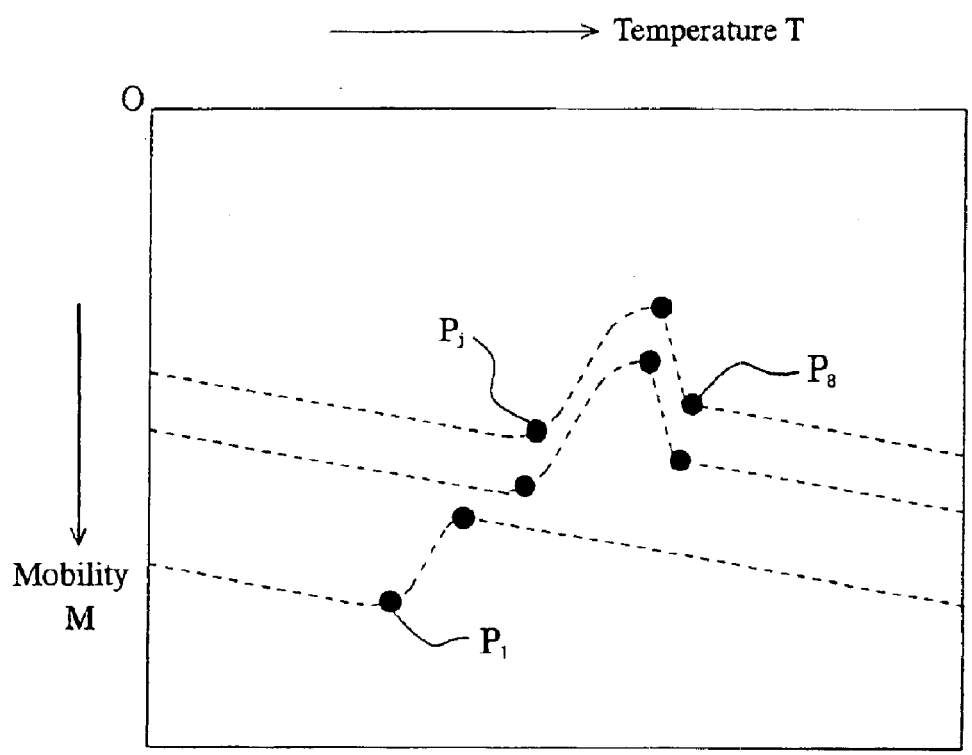
FIG. 4 illustrates eight featuring points $P_j$ (j=1–8) which were extracted from three band curves.

The above-mentioned featuring points extraction is carried out one by one from a clear band, i.e., a clearly subdivided band curve to give a predetermined number of featuring points as a whole. In case the species of a specimen microorganism is already known, and specific bands whose featuring points should be extracted are evident, featuring pints of these specific bands are extracted. FIG. 4 illustrates eight featuring points $P_j$ (j=1–8) which were extracted from three band curves. Actually, eight featuring points or more are extracted from three band curves or more.

Although featuring points are extracted from band curves which were obtained via slimming and functionalization in the above-mentioned description, featuring points can also be extracted directly from each bold line without slimming or functionalization.

(4) Determination of PaSS and/or Genome Semi-distance from Identification Dots (temperature and mobility)

'PaSS' stands for Pattern Similarity Score. 'Genome semi-distance' is an index which expresses a similarity of genomes of two microorganisms using PaSS, and is expressed as (1–PaSS)/PaSS. PaSS and genome semi-distance are determined from featuring points (spiddos) which were obtained by the above-mentioned extraction as described below. A microorganism can be identified by means of genotype using PaSS and/or genome semi-distance. A microorganism is identified by comparing featuring points which were obtained with a genome of a microorganism of interest with those of reference genome.

In case the species of a microorganism of interest is already known, the species is used as the reference.

In case the species of a microorganism of interest is unknown, representative species (e.g., several tens species) which were previously chosen based on the overall shape of the genome profiling image are used as tentative references.

In case the species of a specimen microorganism is unknown, species are successively listed up which have similar featuring points with respect to each featuring point which was obtained by the above-mentioned featuring point extraction (e.g., the difference in distance from starting point O to each featuring point is 5% or less in FIG. 7), and the species which were listed up are assumed to be tentative references.

Then, based on featuring points of reference genomes, corresponding featuring points (e.g., ten dots) are determined from the featuring points which were obtained by the above-mentioned featuring points extraction, wherein 'corresponding featuring points' means featuring points which locally correspond to each of featuring points of reference genomes. Corresponding featuring points can be determined, for example, by 1) 'the operator specification method' in which an operator manually specifies corresponding featuring points one by one on a computer display, 2) 'the automatic assignment method' in which a coordinate zone (a region which occupies a two-dimensional specific area in XY coordinate) is determined to which each of featuring points of reference genomes belongs, and specimen featuring points which belong to the coordinate zone are successively and automatically assigned as corresponding featuring points, 3) 'the optimally corresponding automatic calculation method' in which the number of corresponding featuring points are appropriately set, and featuring points are arbitrarily chosen from featuring points of reference genomes and extracted specimen featuring points so that the number of the featuring points can be each of the numbers of corresponding featuring points, and they are associated according to the combination theory, and corresponding featuring points are automatically determined based on the combination which gives the largest PaSS which is to be defined later.

Figure 5:
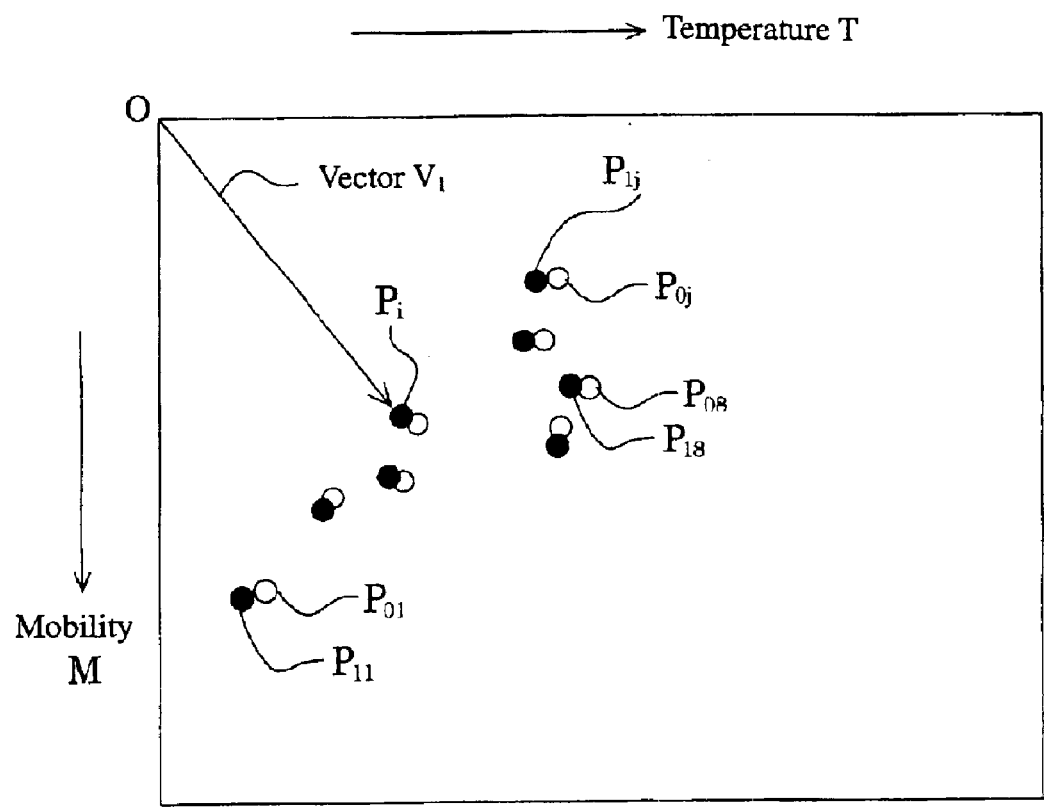
FIG. 5 illustrates 'n' featuring points $P_{1i}$ (i=1–n) with respect to a specimen microorganism which corresponds to 'n' featuring points $P_{0i}$ (i=1–n) with respect to a reference genome.

In this way, as shown in FIG. 5, 'n' featuring points $P_{1i}$ (i=1–n) of a specimen microorganism are obtained corresponding to 'n' featuring points $P_{0i}$ (i=1–n) of a reference genome, wherein each featuring point $P_i$ ('n' featuring points $P_{0i}$ and 'n' featuring points of a specimen microorganism) has position vector $V_i$ (position vector $V_{0i}$ of 'n' featuring points of a reference genome and position vector $V_{1i}$ of 'n' featuring points of a specimen microorganism). Point O at which T=the lowest temperature at M=0 can be used as the starting point of position vector $V_i$.

Using position vector $V_i$ of each featuring point $P_i$, PaSS is obtained which is defined by Eq.1 below:

$$\text{PaSS} = 1 - \{\Sigma \gamma(i)\}/n \tag{1}$$

where 'Σ' denotes the sum of i=1–n, and γ(i) is expressed by Eq.2 below:

$$\gamma(i) = 2 \times |V_{1i} - V_{0i}|/(|V_{1i}| + |V_{0i}|) \tag{2}$$

Although a value of PaSS is determined according to the vector (dependent) type calculation method in the above-mentioned description, the value can also be determined based on the scalar type calculation method as describe below:

$$\text{PaSS} = 1 - \{\Sigma r(i)\}/n \tag{4}$$

where 'Σ' denotes the sum of i=1–n, and r(i) is expressed by Eq.5 below:

$$r(i) = [[T_{1i} - T_{0i})/(T_w/\alpha)]^2 + [(M_{1i} - M_{0i})/(M_{1i} + M_{0i})/2]^2]^{1/2}/(\alpha^2 + 1^2)^{1/2} \tag{5}$$

where '$T_{0i}$' denotes a temperature of 'n' featuring points $P_{0i}$ of a reference genome, and '$T_{1i}$' denotes a temperature of 'n' featuring points $P_{1i}$ of a specimen organism. '$M_{0i}$' denotes the mobility of 'n' featuring points $P_{0i}$ of a reference genome, and '$M_{1i}$' denotes the mobility of 'n' featuring points $P_{1i}$ of a specimen organism. '$T_w$' denotes the temperature normalization factor which corresponds to a temperature range (e.g., about 60° C.) which gives featuring points. 'α' denotes a relative value of both 'weights' of mobility change and temperature change, and is normally 1. Denominator part $(\alpha^2 + 1^2)^{1/2}$ in Eq.5 constitutes the second normalization factor (so that an r(i) value can be 1 or less).

Using PaSS which is obtained based on Eq.1 or 4, genome semi-distance $d_s$ is obtained which is defined by Eq.3 below:

$$d_s = (1 - \text{PaSS})/\text{PaSS} \tag{3}$$

In general, in case the species of a specimen microorganism is the same as that of a reference genome, a PaSS value (score) becomes nearly 1, and a genome semi-distance $d_s$ value becomes nearly 0.

(5) Identification of Microorganism Based on PaSS and/or Genome Semi-distance

In case a species of a microorganism of interest is unknown, PaSS, and if necessary, genome semi-distance $d_s$ is/are calculated for each reference genome. Then, comparison with other reference genome is repeated until a PaSS value goes over a standard value (e.g., 0.96) or a genome semidistance $d_s$ value goes below a standard value (e.g., 0.04). In this way, a species of a specimen microorganism can be identified based on a PaSS value or a genome semi-distance $d_s$ value.

On the other hand, in case the species of a microorganism which is to be identified is known, similarity between individuals can be determined which belong to the same species based on a PaSS or genome semi-distance $d_s$ value. Namely, PaSS or genome semi-distance $d_s$ is determined for two specimen microorganisms which belong to the same species, and in case two PaSS values are adequately near or two genome semi-distance $d_s$ values are adequately near, it is determined that the two specimen microorganisms belong to the same species and similarity between the individuals is high.

In addition, it is preferable to store by plotting a set of species or individuals which exist within a specific genome semi-distance in the genome sequence space as neighboring information.

In this way, it is preferable to resister genome profiling images, featuring points, judgment information, neighboring information, and so on as an appropriate data base, and constitute them so as to be available at any time.

As described above, a melting initiation point which corresponds to the initiation of melting before denaturation, a minimal mobility point where the mobility reaches the minimum before strand dissociation, and a mobility end point where a DNA first reaches the mobility in a single-stranded state after denaturation are extracted as featuring points from a genome profiling imaged. As a result, by a quantitative method using the obtained featuring points, a species of a microorganism and similarity between individuals which are classified into the same species of microorganism can be accurately and simply identified.

A method for identifying a species of and a method for identifying similarity of a microorganism by its genotype are described above. A method according to the present invention is not limited to a microorganism, but is also applicable to methods for identification such as a method for identifying a species of and a method for identifying similarity of a general organism.

EXAMPLES

The present invention will be described in more detail by examples below.

Example 1

Genome profiling (GP) according to the present invention of strains of yeasts, *Escherichia coli*, and *Bacillus subtilis*, and mutants therefrom (twenty kinds as a whole) was carried out as described below, and their spiddos were determined with a computer, and were registered as a database. *Bacillus subtilis* was newly isolated from commercially available natto, and DNA was extracted, and GP was carried out to give spiddos, which were assumed as spiddos of a tentative unknown specimen X.

Preparation of Double-stranded DNA Fragment by Random PCR

One hundred µl of reaction mixture which contains 200 µM dNTP (N=G, A, T, C), 0.5 µM primer(pfM12 (dAGAACGCGCCTG) (SEQ ID NO: 39)) 10 mM Tris-HCl (pH 9.0), 50 mM KCl, 2.5 mM $MgCl_2$, 0.1% Triton X-100, 0.02 unit/µl Taq DNA polymerase, and an appropriate amount of template DNA (3 µl of a DNA solution was added, and the volume of the reaction mixture was adjusted to 100 µl ) was prepared for each DNA. Double-stranded DNA fragments were prepared by PCR comprising the steps of 1) the treatment at 94° C. for 1 min, 2) 20–30 times repeating the cycle comprising denaturation at 94° C. for 30 min, annealing at 28° C. for 2 min, and elongation at 47° C. for 2 min, followed by 3) the treatment at 47° C. for 2 min.

TGGE of Double-stranded DNA Fragment

To the double-stranded DNA fragment which was obtained as described above, 0.3 µg of DNA which has SEQ ID No.1 was added as standard DNA, and TGGE was carried out. Condition for TGGE is as follows: 4% polyacrylamide gel (40 mM Tris buffer (pH 8.0) which contains 8M urea), linear temperature gradient from 30 to 70° C., 400V, 110 min, Taitec electrophoresis apparatus TG-180.

Extraction of Identification Dots of Each DNA Fragment from Electrophoresis Pattern A band (electrophoresis pattern) of DNA (including standard DNA) on an electrophoresis gel which was obtained by TGGE was silver stained as described below, and identification dots were extracted from each visualized pattern.

1) A gel which is attached to a gel bond film is directly transferred into a plastic container which contains 200 ml of a 30% PEG 2000 aqueous solution, and stirred at room temperature (15–30° C.) for 30 min. Meanwhile, the gel is detached from the film, contracted, and becomes white and translucent.
2) The solution is once substituted for 150 ml of distilled water, and the gel is adequately rinsed. This procedure is repeated again. Rinsed water is absolutely sucked with an aspirator.
3) After the rinsed water is removed, about 200 ml of a silver stain solution (which was prepared by adding 10 ml of 1M NaOH and 2 ml of 25% ammonia aqueous solution to 200 ml of bidistilled water, mixing, followed by dissolving 0.4 g of silver nitrate) is added, and stirred for 30 min.
4) The liquid is substituted for 200 ml of bidistilled water, and stirred for 1 min, and the water is discarded. This procedure is repeated again.
5) The liquid is substituted for about 200 ml of a developer (which was prepared by adding 200 µl of 10% citric acid and 200 µl of formalin to 200 ml of bidistilled water, followed by dissolving), and gently shaken until a band is appropriately stained.
6) When the band is appropriately stained, the developer is quickly removed, and 200 ml of a previously prepared stop solution (10% acetic acid+40% methanol, in water) is added, and stirred for about 10 min to give a stained gel specimen.

Featuring points were extracted from each pattern which was visualized by the above-mentioned method, and spiddos were determined. Identification dots were extracted as follows:

A gel picture of GP was imported into a computer with a scanner, and the obtained image was corrected and normalized with a computer, and identification dots were extracted by a method how featuring points were specified for an image on a display with a mouse.

The spiddos which were obtained in this way of an unknown specimen were compared with ten spiddos of various genomes on a data base, and PaSS was calculated by the total combination calculation method.

A genome which gives the highest PaSS with X was automatically extracted from 20 kinds of genomes which were previously registered.

Results were obtained as a computer output, and accompanying information revealed that the organism which X showed the highest similarity is *Bacillus subtilis*.

Example 2

Figure 6:
FIG. 6a illustrates an electrophoresis pattern in case cy3-pfM12 (5' cy3-AGA ACG CGC CTG 3') (SEQ ID NO: 4) which was obtained in Example 2 was used as a primer.
FIG. 6b illustrates an electrophoresis pattern in case FITC/UCS (5' FTTC-CA GGA AAC AGC TAT GAC 3') (SEQ ID NO: 38)was used as a primer.

Random PCR was carried out under the same condition except using DNA of *Bacillus subtilis* as a template, and cy3-pfM12 (5' cy3-AGA ACG CGC CTG 3') (SEQ ID NO: 4) which contains phosphor cy3 or FITC/UCS (5' FITC-CAGGAAACGGCTATGGAC3') (SEQ ID NO: 40) which contains phosphor FITC as a primer for each primer, and the obtained double-stranded amplified DNA fragments were mixed, and TGGE was carried out in a way which is similar to Example 1. An electrophoresis pattern by TGGE was visualized with an excitation/fluorescent wavelength of 550 nm/570 nm (phosphor cy3) or 494 nm/519 nm (phosphor FITC). FIG. 6a illustrates an electrophoresis pattern in the case where cy3-pfM12 (5'cy3-AGAACGCGCCTG3') (SEQ ID NO: 4) was used as a primer, and FIG. 6b illustrates an electrophoresis pattern in the case where FITC/UCS (5' FITC-CAGGAAACAGCTATGAC3') was used as a primer. Identification dots were extracted form each pattern. The microorganism which was used as a template was identified as *Bacillus subtilis* based the obtained identification dots.

The present disclosure relates to the subject matter contained in Japanese Patent Application No. 2000-123755, filed on Apr. 25, 2000, which is expressly incorporated herein by reference in its entirely.

While illustrative and presently preferred embodiments of the present invention have been described in detail herein, it is to be understood that the inventive concepts may be otherwise variously embodied and employed and that the appended claims are intended to be construed to be construed to include such variations except insofar as limited by the prior art.

What is claimed is:

1. A method for determining the similarity at the genome level between a target organism and a reference organism comprising the steps of:
   a) preparing one or more of double-stranded DNA fragments by random PCR using, as a template, genome DNA of the target organism,
   b) subjecting said double-stranded DNA fragments prepared in step a) to temperature gradient gel electrophoresis (TGGE) or denaturant gradient gel electrophoresis (DGGE), wherein an internal reference double-stranded DNA prepared in advance, is co-migrated with the double-stranded DNA fragments,
   c) assigning each melting initiation point and/or each mobility transition end point of the double-stranded DNA fragments prepared in step a) and both the melting initiation point and the mobility transition end point of the internal reference double-stranded DNA co-migrated from an electrophoretic pattern obtained in step b), d) normalizing each coordinate of melting initiation point and/or mobility transition end point of the double-stranded DNA fragments using those of the melting initiation point and mobility transition end point of the internal reference double-stranded DNA to eliminate experimental fluctuations and generate species identification dots, e) calculating PaSS (Pattern Similarity Score) defined by equation 1 below:

$$\text{PaSS} = 1 - \{\Sigma \gamma(i)\}/n \quad (1)$$

where '$\Sigma$' denotes the summation over i=1 to n (where n is the number of the species identification dots used for the calculation), and $\gamma(i)$ is expressed by equation 2 below:

$$\gamma(i) = 2 \times |V_{1i} - V_{0i}| / (|V_{1i}| + |V_{0i}|) \quad (2)$$

where $V_{0i}$ represents position vector of the i-th species identification dots of the reference organism and $V_{1i}$ represents position vector of the i-th species identification dots of the target organism;

using species identification dots obtained in step d) and species identification dots of the reference organism to determine the similarity at the genome level between the target organism and the reference organism, wherein the species identification dots of the reference organism is separately obtained by a method in which steps a) to d) are carried out under the same conditions.

2. A method according to claim 1, wherein said standard DNA is SEQ ID NO: 1 or SEQ ID NO: 2.

3. A method according to claim 1, wherein said identification of an organism is the species identification or homology identification of an organism.

4. A method according to claim 1, wherein in step a), a primer or nucleotide labeled with a fluorescent marker is used for said random PCR to amplify DNA fragments with a fluorescent marker and a fluorescence labeled DNA is used as the standard DNA, and in step c), said extraction from the featuring points is carried out by image processing using the fluorescent markers carried by the DNAs.

5. A method according to claim 1, wherein the featuring points which are obtained in step c) are expressed by the coordinates of the temperature axis and the mobility axis in the case of temperature gradient gel electrophoresis (TGGE), and by the coordinates of the denaturant concentration axis and the mobility axis in the case of denaturant gradient gel electrophoresis (DGGE).

6. A method according to claim 1, wherein said organism is a microorganism.

7. A method for identifying a reference organism closest at the genome level to a target organism comprising the steps of:
a) preparing one or more of double-stranded DNA fragments by random PCR using, as a template, genome DNA of the target organism,
b) subjecting said double-stranded DNA fragments prepared in step a) to temperature gradient gel electrophoresis (TGGE) or denaturant gradient gel electrophoresis (DGGE), wherein an internal reference double-stranded DNA prepared in advance, is co-migrated with the double-stranded DNA fragments,
c) assigning each melting initiation point and/or each mobility transition end points of the double-stranded DNA fragments prepared in step a) and both the melting initiation point and the mobility transition end point of the internal reference double-stranded DNA co-migrated from an electrophoretic pattern obtained in step b),
d) normalizing each coordinate of melting initiation point and/or mobility transition end point of the double-stranded DNA fragments using those of the melting initiation point and/or mobility transition end point of the internal reference double-stranded DNA to eliminate experimental fluctuations and generate species identification dots,
e) calculating PaSS (Pattern Similarity Score) defined by equation 1 below:

$$\text{PaSS} = 1 - \{\Sigma \gamma(i)\}/n \quad (1)$$

where '$\Sigma$' denotes the summation over i=1 to n (where n is the number of the species identification dots used for the calculation), and $\gamma(i)$ is expressed by equation 2 below:

$$\gamma(i) = 2 \times |V_{1i} - V_{0i}| / (|V_{1i}| + |V_{0i}|) \quad (2)$$

where $V_{01}$ represents position vector of the i-th species identification dots of the reference organism and $V_{1i}$ represents position vector of the i-th species identification dots of the target organism;

using species identification dots obtained in step d) and species identification dots of a reference organism deposited in a database in which species identification dots of organisms separately determined by a method in which steps a) to d) are carried out under the same conditions are registered, and f) repeating calculation of PaSS of step e) with altering the reference organism until the maximum PaSS is reached to identify the reference organism closest at the genome level to the target organism.

8. A method according to claim 7, wherein said standard DNA is SEQ ID NO: 1 or SEQ ID NO: 2.

9. A method according to claim 7, wherein said identification of an organism is the species identification or homology identification of an organism.

10. A method according to claim 7, wherein in step a), a primer or nucleotide labeled with a fluorescent marker is used for said random PCR to amplify DNA fragments with a fluorescent marker and a fluorescence labeled DNA is used as the standard DNA, and in step c), said extraction from the featuring points is carried out by image processing using the fluorescent markers carried by the DNAs.

11. A method according to claim 7, wherein the featuring points which are obtained in step c) are expressed by the coordinates of the temperature axis and the mobility axis in the case of temperature gradient gel electrophoresis (TGGE), and by the coordinates of the denaturant concentration axis and the mobility axis in the case of denaturant gradient gel electrophoresis (DGGE).

12. A method according to claim 7, wherein said organism is a microorganism.

13. A method for determining the similarity at the genome level between a target organism and a reference organism comprising the steps of:
a) preparing one or more of double-stranded DNA fragments by random PCR using, as a template, genome DNA of the target organism,
b) subjecting said double-stranded DNA fragments prepared in step a) to temperature gradient gel electrophoresis (TGGE) or denaturant gradient gel electrophoresis (DGGE), wherein an internal reference double-stranded DNA prepared in advance, is co-migrated with the double-stranded DNA fragments, c) assigning each melting initiation point and/or each mobility transition end point of the double-stranded DNA fragments prepared in step a) and both the melting initiation point and the mobility transition end point of the internal reference double-stranded DNA co-migrated from an electrophoretic pattern obtained in step b), d) normalizing each coordinate of melting initiation point and/or mobility transition end point of the double-stranded DNA fragments using those of the melting initiation point and mobility transition end point of the internal reference double-stranded DNA to eliminate experimental fluctuations and generate species identification dots, e) calculating genome semi-distance by the formula $$(1-\text{Pass})/\text{Pass}$$

to determine the similarity at the genome level between the target organism and the reference organism, PaSS (Pattern Similarity Score) defined by equation 1 below:

$$\text{PaSS}=1-\{\Sigma\gamma(i)\}/n \quad (1)$$

where 'Σ' denotes the summation over i=1 to n (where n is the number of the species identification dots used for the calculation), and γ(i) is expressed by equation 2 below:

$$\gamma(i)=2\times|V_{1i}-V_{0i}|/(|V_{1i}|+|V_{0i}|) \quad (2)$$

where $V_{0i}$ represents position vector of the i-th species identification dots of the reference organism and $V_{1i}$ represents position vector of the i-th species identification dots of the target organism;

using species identification dots obtained in step d) and species identification dots of the reference organism to determine the similarity at the genome level between the target organism and the reference organism, wherein the species identification dots of the reference organism is separately obtained by a method in which steps a) to d) are carried out under the same conditions.

14. A method according to claim 13, wherein said standard DNA is SEQ ID NO: 1 or SEQ ID NO: 2.

15. A method according to claim 13, wherein said identification of an organism is the species identification or homology identification of an organism.

16. A method according to claim 13, wherein in step a), a primer or nucleotide labeled with a fluorescent marker is used for said random PCR to amplify DNA fragments with a fluorescent marker and a fluorescence labeled DNA is used as the standard DNA, and in step c), said extraction from the featuring points is carried out by image processing using the fluorescent markers carried by the DNAs.

17. A method according to claim 13, wherein the featuring points which are obtained in step c) are expressed by the coordinates of the temperature axis and the mobility axis in the case of temperature gradient gel electrophoresis (TGGE), and by the coordinates of the denaturant concentration axis and the mobility axis in the case of denaturant gradient gel electrophoresis (DGGE).

18. A method according to claim 13, wherein said organism is a microorganism.

19. A method for identifying a reference organism closest at the genome level to a target organism comprising the steps of:

a) preparing one or more of double-stranded DNA fragments by random PCR using, as a template, genome DNA of the target organism, b) subjecting said double-stranded DNA fragments prepared in step a) to temperature gradient gel electrophoresis (TGGE) or denaturant gradient gel electrophoresis (DGGE), wherein an internal reference double-stranded DNA prepared in advance, is co-migrated with the double-stranded DNA fragments, c) assigning each melting initiation point and/or each mobility transition end points of the double-stranded DNA fragments prepared in step a) and both the melting initiation point and the mobility transition end point of the internal reference double-stranded DNA co-migrated from an electrophoretic pattern obtained in step b), d) normalizing each coordinate of melting initiation point and/or mobility transition end point of the double-stranded DNA fragments using those of the melting initiation point and/or mobility transition end point of the internal reference double-stranded DNA to eliminate experimental fluctuations and generate species identification dots, e) calculating genome semi-distance by the formula $$(1-\text{Pass})/\text{Pass}$$

to determine the similarity at the genome level between the target organism and the reference organism, PaSS (Pattern Similarity Score) defined by equation 1 below:

$$\text{PaSS}=1-\{\Sigma\gamma(i)\}/n \quad (1)$$

where 'Σ' denotes the summation over i=1 to n (where n is the number of the species identification dots used for the calculation), and γ(i) is expressed by equation 2 below:

$$\gamma(i)=2\times|V_{1i}-V_{0i}|/(|V_{1i}|+|V_{0i}|) \quad (2)$$

where $V_{0i}$ represents position vector of the i-th species identification dots of the reference organism and $V_{1i}$ represents position vector of the i-th species identification dots of the target organism;

using species identification dots obtained in step d) and species identification dots of a reference organism deposited in a database in which species identification dots of organisms separately determined by a method in which steps a) to d) are carried out under the same conditions are registered, and f) repeating calculation of genome semi-distance of step e) with altering the reference organism until the maximum genome semi-distance is reached to identify the reference organism closest at the genome level to the target organism.

20. A method according to claim 19, wherein said standard DNA is SEQ ID NO: 1 or SEQ ID NO: 2.

21. A method according to claim 19, wherein said identification of an organism is the species identification or homology identification of an organism.

22. A method according to claim 19, wherein in step a), a primer or nucleotide labeled with a fluorescent marker is used for said random PCR to amplify DNA fragments with a fluorescent marker and a fluorescence labeled DNA is used as the standard DNA, and in step c), said extraction from the featuring points is carried out by image processing using the fluorescent markers carried by the DNAs.

23. A method according to claim 19, wherein the featuring points which are obtained in step c) are expressed by the coordinates of the temperature axis and the mobility axis in the case of temperature gradient gel electrophoresis (TGGE), and by the coordinates of the denaturant concentration axis and the mobility axis in the case of denaturant gradient gel electrophoresis (DGGE).

24. A method according to claim 19, wherein said organism is a microorganism.

* * * * *

SEQUENCE LISTING

<160> NUMBER OF SEQ ID NOS: 44

<210> SEQ ID NO 1
<211> LENGTH: 204
<212> TYPE: DNA

-continued

```
<213> ORGANISM: Unknown Organism
<220> FEATURE:
<223> OTHER INFORMATION: Description of Unknown Organism: Illustrative
      standard DNA

<400> SEQUENCE: 1
tgctacgtct cttccgatgc tgtctttcgc tgctgagggt gacgatcccg caaaagcggc    60
ctttgactcc ctgcaagcct cagcgaccga atatatcggt tatgcgtggg cgatggttgt   120
tgtcattgtc ggcgcaacta tcggtatcaa gctgtttaag aaattcacct cgaaagcaag   180
ctgataaacc gatagaattc aagg                                          204

<210> SEQ ID NO 2
<211> LENGTH: 286
<212> TYPE: DNA
<213> ORGANISM: Unknown Organism
<220> FEATURE:
<223> OTHER INFORMATION: Description of Unknown Organism: Illustrative
      standard DNA

<400> SEQUENCE: 2
attggcgcgc tggcaacgat tgcccgtgcg caaggcggcg taatgcgtca tgtcaaaccg    60
cacggcatgt tgtacaacca ggcggcgaaa gaagcacaac tggcagacgc catcgccaga   120
gcggtatacg cttgcgatcc agcattgatt ctcgtcgggc tggcgggaag cgagctgatt   180
cgtgcaggca agcaatatgg tctgacaacg cgcgaggaag tgtttgccga tcgcggttat   240
caggctgacg gctcgctggt gccgcgaagc cagtcaggcg cgttga                  286

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 3
cagtcaggac gt                                                        12

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 4
agaacgcgcc tg                                                        12

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 5
cgtcgctatt aa                                                        12

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Primer
```

```
<400> SEQUENCE: 6
cagggcgcgt ac                                                          12

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: Primer

<400> SEQUENCE: 7
aaaaaaaaaa a                                                           11

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 8
aaatttaaat tt                                                          12

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 9
aattaattaa tt                                                          12

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 10
acgacgacga cg                                                          12

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 11
atatatatat at                                                          12

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 12
cccccccccc cc                                                          12

<210> SEQ ID NO 13
```

```
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 13
ccggccggcc gg                                                             12

<210> SEQ ID NO 14
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 14
ctctctctct ct                                                             12

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 15
gggggggggg gg                                                             12

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 16
gagagagaga ga                                                             12

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 17
ggccggccgg cc                                                             12

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 18
tttttttttt tt                                                             12

<210> SEQ ID NO 19
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 19
```

```
tttgggtttg gg                                                              12
```

<210> SEQ ID NO 20
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 20

```
tgctgctgct gc                                                              12
```

<210> SEQ ID NO 21
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 21

```
tatatatacc ac                                                              12
```

<210> SEQ ID NO 22
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 22

```
gggcggcgac ct                                                              12
```

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 23

```
aggtcgccgc cc                                                              12
```

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 24

```
ggggtcgagg gg                                                              12
```

<210> SEQ ID NO 25
<211> LENGTH: 11
<212> TYPE: DNA
<213> ORGANISM: Artificial Sequence
<220> FEATURE:
<223> OTHER INFORMATION: Description of Artificial Sequence: Primer

<400> SEQUENCE: 25

```
gctaaaaaaa a                                                               11
```

<210> SEQ ID NO 26
<211> LENGTH: 12
<212> TYPE: DNA

```
<213> ORGANISM: Artificial Sequence
<220> FEATURE:
<223> OTHER INFORMATION: Description of Artificial Sequence: Primer

<400> SEQUENCE: 26
caattctaca ac                                                              12

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 27
acgagcgagc gc                                                              12

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 28
tataattata at                                                              12

<210> SEQ ID NO 29
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 29
attataatta ta                                                              12

<210> SEQ ID NO 30
<211> LENGTH: 13
<212> TYPE: DNA
<213> ORGANISM: Artificial Sequence
<220> FEATURE:
<223> OTHER INFORMATION: Description of Artificial Sequence: Primer

<400> SEQUENCE: 30
gatcacctcc tta                                                             13

<210> SEQ ID NO 31
<211> LENGTH: 13
<212> TYPE: DNA
<213> ORGANISM: Artificial Sequence
<220> FEATURE:
<223> OTHER INFORMATION: Description of Artificial Sequence: Primer

<400> SEQUENCE: 31
taaggaggtg atc                                                             13

<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 32
cccacccacc ca                                                              12
```

```
<210> SEQ ID NO 33
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 33
tgggtgggtg gg                                                            12

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 34
gaggaaacag ctatgagatc ttctc                                              25

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 35
caggaaacag ctatgacgtt ctcac                                              25

<210> SEQ ID NO 36
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 36
ggcgatatcc ctgaaa                                                        16

<210> SEQ ID NO 37
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 37
tattatttcc gcaaag                                                        16

<210> SEQ ID NO 38
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 38
caggaaacag ctatgac                                                       17

<210> SEQ ID NO 39
<211> LENGTH: 12
<212> TYPE: DNA
<213> ORGANISM: Artificial Sequence
<220> FEATURE:
```

-continued

```
<223> OTHER INFORMATION: Description of Artificial Sequence: Primer

<400> SEQUENCE: 39
agaacgcgcc tg                                                          12

<210> SEQ ID NO 40
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 40
caggaaacag ctatgac                                                     17

<210> SEQ ID NO 41
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 41
tgctacgtct cttccgatgc tgtctttcgc t                                     31

<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 42
tgctacgtct cttccgatgc tgtctttcgc t                                     31

<210> SEQ ID NO 43
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 43
gaacctcccg ac                                                          12

<210> SEQ ID NO 44
<211> LENGTH: 12
<212> TYPE: DNA
<213> ORGANISM: Artificial Sequence
<220> FEATURE:
<223> OTHER INFORMATION: Description of Artificial Sequence: Primer

<400> SEQUENCE: 44
tgctgctgct gc                                                          12
```